United States Patent [19]

Ernst

[11] 4,182,162
[45] Jan. 8, 1980

[54] DUROMETER

[76] Inventor: Alfred Ernst, Via San Martina 6, Vezia Ticino, Switzerland

[21] Appl. No.: 890,189

[22] Filed: Mar. 27, 1978

[30] Foreign Application Priority Data

Mar. 25, 1977 [CH] Switzerland ............... 3827/77

[51] Int. Cl.² ............................................. G01N 3/44
[52] U.S. Cl. ............................................. 73/81; 73/83
[58] Field of Search ............................ 73/81, 83, 85

[56] References Cited

U.S. PATENT DOCUMENTS

| 3,593,572 | 7/1971 | Hansen | 73/81 |
| 3,855,848 | 12/1974 | Sidler | 73/81 |

Primary Examiner—Anthony V. Ciarlante
Attorney, Agent, or Firm—Michael J. Striker

[57] ABSTRACT

A durometer is provided. The durometer includes an indentor point for penetrating under pressure of an applied load a surface being tested for hardness. Also included is a load generator, which may be a hydraulic cylinder. A support structure is provided for suspending the durometer's indentor point therefrom. An articulation joint connects the indentor point to support structure. Due to the use of this articulation joint, this invention avoids the deleterious effects generally accompanying transmission of moment from the support structure to the indentor point.

9 Claims, 3 Drawing Figures

DUROMETER

BACKGROUND OF THE INVENTION

The present invention relates to a joint which suspends a durometer and which transmits a load to the durometer.

A durometer is an instrument for measuring hardness and consists essentially of a small drill or blunt indentor point working under pressure (as that exerted by a spring). The hardness of an object is typically determined by comparing the depth of the hole against a standard value when the drill, the number of rotations and the drill pressure are the same.

Conventional durometers, particularly those capable of transmitting a substantial load, are generally rigidly suspended from a support structure. The loading of the durometers is transmitted from load-generating equipment such as a hydraulic cylinder, an electromagnet, a motor, and the like.

Surveys have revealed inaccuracy of results from a large number of machines which are subject to vibration when in use. It seems that the force produced by the pressure-generating equipment causes the support structure to vibrate and consequently results in the tip of the durometer sliding on an object being tested when axial transmission of load is interfered with. This means a defective indentation and consequently inaccurate measurement of hardness.

SUMMARY OF THE INVENTION

An object of the present invention is the elimination of inaccurate measurements due to vibrating rigid support structure.

Inaccurate measurements are at least substantially eliminated by the herein-disclosed structure due to the use of an articulation joint to connect a support structure to an indentor point. The support structure, which suspends the indentor point above a material being tested, is resiliently deformed when load is transmitted through the support structure to the indentor point. These deformations engender eccentric forces which change the orientation of the indentor point relative to the support structure. Consequently the indentor point may slide on the surface of the material due to the indentor point being inclined relative to the supporting structure in an eccentric position which interferes with axially directed transmission of a load to the indentor point. The articulation joint connects the indentor point to the support structure without permitting moment engendered in the support structure to interfere with an accurate measurement of hardness.

Due to the provision of this articulation joint, the durometer indentor point may be angularly repositioned in response to deformations in the support structure which change the axial orientation thereof. Consequently, axial transmission of applied load is maintained free from interfering moment.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
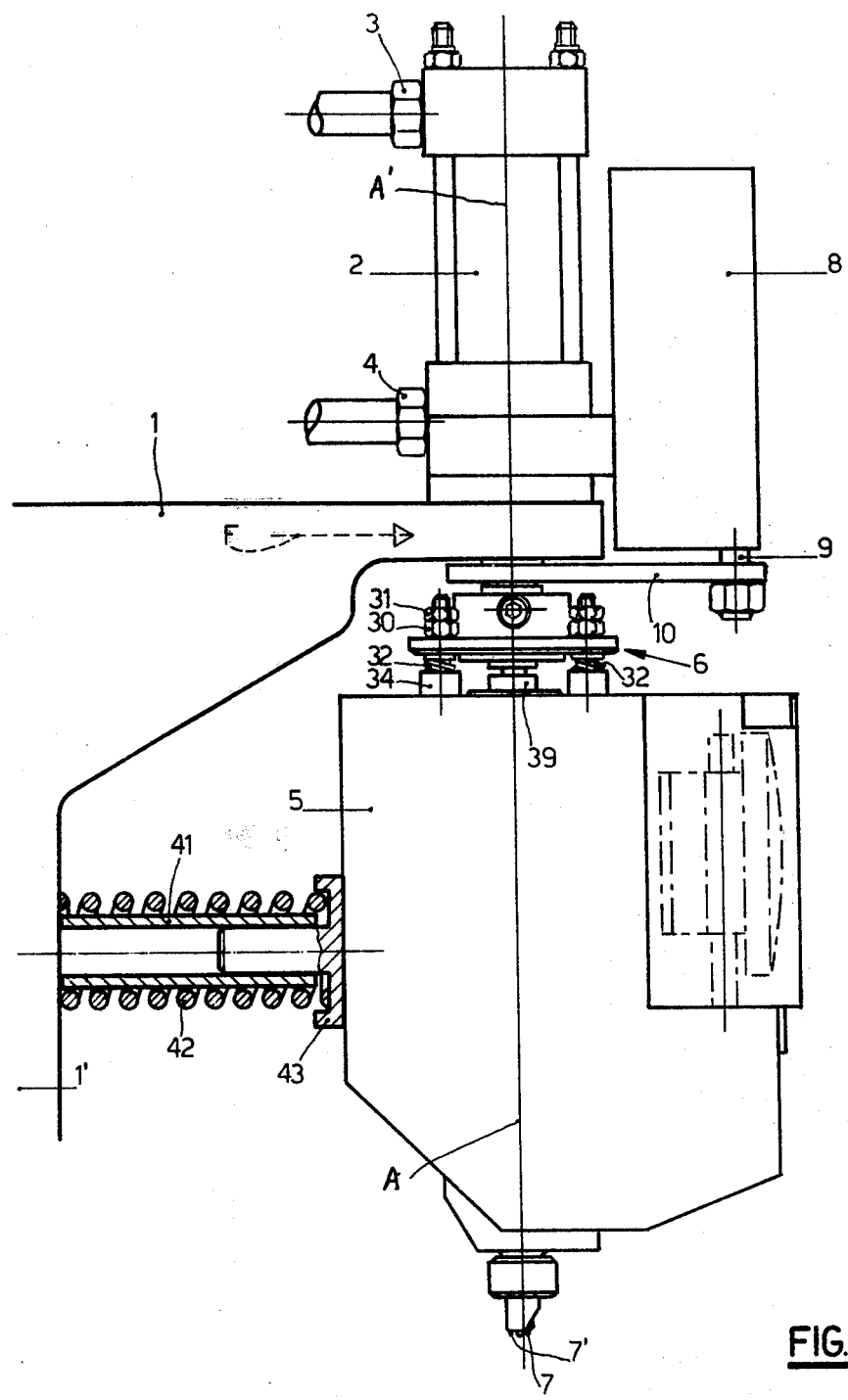
FIG. 1 is a side view of an assembly for testing hardness, the assembly including a durometer, a support structure and a suspension joint for the durometer.

FIG. 1 shows an end portion of a support structure 1. The support structure 1 may be a bracket-type structure for example, but other kinds of structures may be used.

For purposes of convenient description, the term "upwardly" shall be used to describe a direction extending in FIG. 1 from the tip 7 towards the hydraulic cylinder 2. The term "downwardly" shall be used to connote the opposite direction.

Load-generating equipment 2 is also illustrated. The equipment 2 may be a hydraulic cylinder or any other kind of load-generator, such as an electromagnet, a motor with an axially movable rod. Whatever the form of the load-generating equipment, it must direct a load below the supporting structure 1 and along a predetermined direction and distance so as to transmit the load to a durometer 5. The embodiment of FIG. 1 specifically illustrates a double acting hydraulic cylinder 2. The requisite liquid passes through the hydraulic cylinder 2 by way of connections 3 and 4.

The hydraulic cylinder 2 has a plunger 11 which is capable of exerting an axial thrust below the support structure 1 so as to transmit an "applied load" to the durometer 5.

The durometer 5 has a conventional internal structure. The durometer is brought into contact with a surface under test and commonly a "minor" load is applied as a reference load. This permits calibration relative to a basic reference point. Then a "major" load is applied to bring the total load up to the required maximum. The "major" load is maintained until the surface under test stops creeping. The "major" load is then removed to permit elastic recovery while maintaining the "minor" load.

As shown in FIG. 1, the durometer 5 is located below the support structure 1. FIG. 1 shows the durometer 5 arranged in such a manner that its axis A and the penetrator tip or indentor point 7 of the durometer 5 are aligned with the axis A' of the hydraulic cylinder 2 so that axis A and A' together form a single axis. However, such perfect superposition is not necessary; the axis A of the durometer 5 may be displaced relative to the axis A' of the hydraulic cylinder 2—provided that the axes are at least substantially parallel.

Rod 9 and plate 10 have the double function of preventing rotation of the plunger 11 of the cylinder around axis A' and of limiting the upward return of the plunger. This second function is performed by their actuation of a conventional microswitch (unillustrated).

Guide casing 8 is located at a side of cylinder 2 and has the function of orienting the rod 9 so that it is parallel to the axis A' of the cylinder 2. The opposite end of rod 9 is connected to one end of the horizontal plate 10. The opposite end of horizontal plate 10 is tightened around the plunger 11 of cylinder 2.

Figure 2:
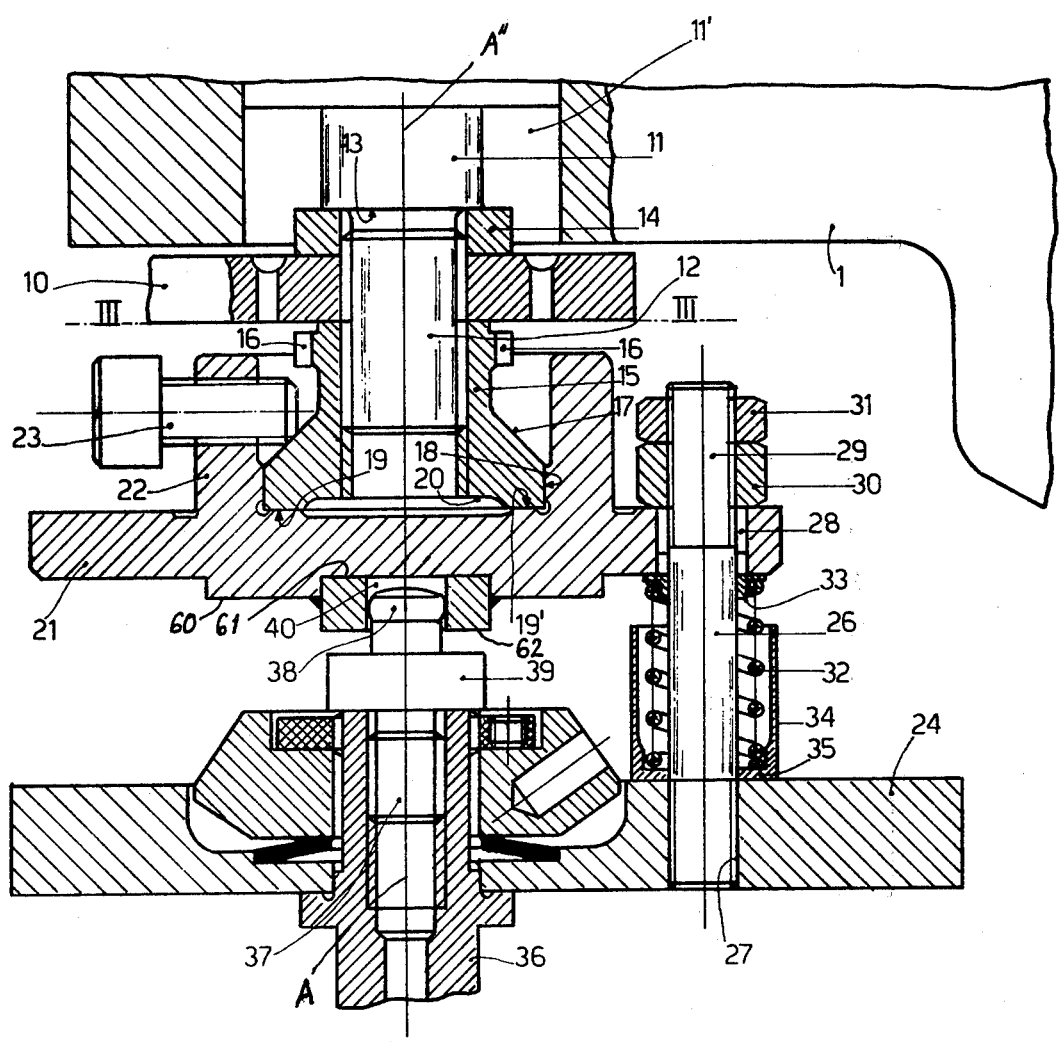
FIG. 2 is a cross-section of the suspension joint, the cross-section being taken on line II—II of FIG. 3.

FIG. 2 shows support structure 1 with a large aperture 11' passing therethrough. Plunger 11 of cylinder 2 passes through aperture 11'. Plunger 11 has a threaded portion 12 which projects below the support structure 1. Threaded portion 12 has a reduced diameter relative to the upper portion 11; this reduced diameter forms a shoulder 13.

A spacer ring 14 is located around threaded portion 12 in such a manner that the spacer ring 14 abuts the shoulder 13. The horizontal plate 10 also fits about the threaded portion 12 and abuts the opposite, downwardly facing side of the spacer ring 14. Ring nut 15 is twisted onto threaded portion 12 at a location below the horizontal plate 10. Ring nut 15 has two opposite notches 16 for pressing the ring nut 15 tightly against horizontal plate 10 and spacer ring 14.

At its downwardly facing, opposite end, the ring nut 15 is formed with a frustoconical portion 17 which effectively widens the diameter of the lower part of the ring nut 15. The frustoconical portion 17 extends radially outwardly from the threaded portion 12 so as to form a cylindrical portion 18 which has a downwardly facing planar face 19, planar face 19 being perpendicular to axis A' of the threaded portion 12 of plunger 11. The planar face 19 is recessed so as to form an annular, radially extending recess 20 within the planar face.

Flange 21 is a plate-like body formed with a cylindrical wall 22 extending perpendicularly to the plate-like portion of flange 21. The inner diameter of cylindrical wall 22 is equal to the outer diameter of the cylindrical section 18—the cylindrical wall 22 receives cylindrical section 18 without play. As illustrated in FIG. 2, cylindrical wall 22 has a planar bottom surface designed to match that of the cylindrical section 18 so that planar surfaces 19 and 19' closely engage each other to thereby stabilize the coaxial position of flange 21 when fitted over the plunger 11. In its position over the threaded portion 12, the base portion of flange 21 extends radially from axis A' while cylindrical wall 22 is parallel to axis A'. The base portion of flange 21 extends radially beyond cylindrical wall 22. Preferably a downwardly extending cylindrical portion 60 projects from the base portion 21.

Preferably, three radially extending screws 23 lock the flange 21 on the ring nut 15. Each screw 23 preferably extends through cylindrical wall 22 and is positioned with its inwardly directed end being pressed on the conical portion 17 of ring nut 15 in order to maintain a secure engagement of flange 21 and ring nut 15. Due to the fact that ring nut 15 is threaded onto threaded portion 12 of plunger 11, and due to the locking engagement of ring nut 15 and flange 21, flange 21 is consequently rigidly connected to plunger 11 and is jointly axially displaceable therewith.

FIG. 2 also shows horizontal plate 24. Three threaded axial holes 27 extend therethrough, and a bolt 26 is extended upwardly through each hole 27. The holes 27 are preferably circumferentially, equidistantly spaced from each other. Horizontal plate 24 is connected to durometer 5 via screws 25 (see FIG. 3).

Flange 21 has three holes 28 which are each superimposable over one of the respective holes 27. Bolts 26 extend upwardly through and beyond a respective one of the holes 28.

Each hole 28 is larger than each bolt 26 so that each bolt 26 fits loosely therein and is therefore free to be angularly repositioned while remaining within a respective one of the holes 28.

A screw nut 30 and a lock nut 31 are secured to this upwardly extending end of each bolt 26. Nuts 30 and 31 preferably abut each other.

Each screw nut 30 abuts the upwardly directed surface of that part of the base portion of flange 21 which extends radially beyond cylindrical wall 22. Consequently, plate 24 is supported by flange 21 on the bolts 26. On the other hand, the plate 24 is axially displaceable relative to flange 21 due to axial slidability of plate 24 along bolts 26 and due to the loose fitting of the bolts within the holes 28.

A coil spring 32 is wound around each bolt 26 and is pressed between flange 21 and plate 24.

An annular neck 33 is positioned on the lower surface of flange 21 around each hole 28, and a sleeve 34 with a bottom 35 is positioned on the upper surface of plate 24. Each coil spring 32 extends between neck 33 and bottom 35 so as to abut each and press them against the respective surfaces. The function of coil springs 32 is to maintain spacing between plate 24 and flange 21.

Nuts 30 and 31 are screwable or unscrewable so that the axis of the durometer 5 can be oriented relative to axis A'—either coaxially or parallel. Tightening or loosening these nuts 30, 31 also functions to compress or decompress the coil springs 32.

The minor load or preload applied to the durometer 5 functions to retard swinging of the durometer 5 relative to the flange 21. Still the accumulated preload transmitted by springs 32 is only a fraction of the later-applied major load. If the total load to be applied is for example, 150 kg., the entire preload may advantageously amount to only 20–30 kg.

Flange 21 is rigid. Bolts 26 constitute the suspension for the durometer 5 as well constituting the guide means of the durometer 5. The screw nuts 30 and lock nuts 31 provide the detent which defines a single orientation position of axis A of the durometer 5 relative to axis A' of the plunger 11. Coil springs 32 constitute the resilient means which maintain or restore an axially displaced durometer to the orientation position. A single orientation position is important to maintain uniform circumstances of load transmission to the indentor point 7, if load is initially axially applied and then the indentor point changes orientation relative to the support structure, inaccurate measurements result.

Figure 3:
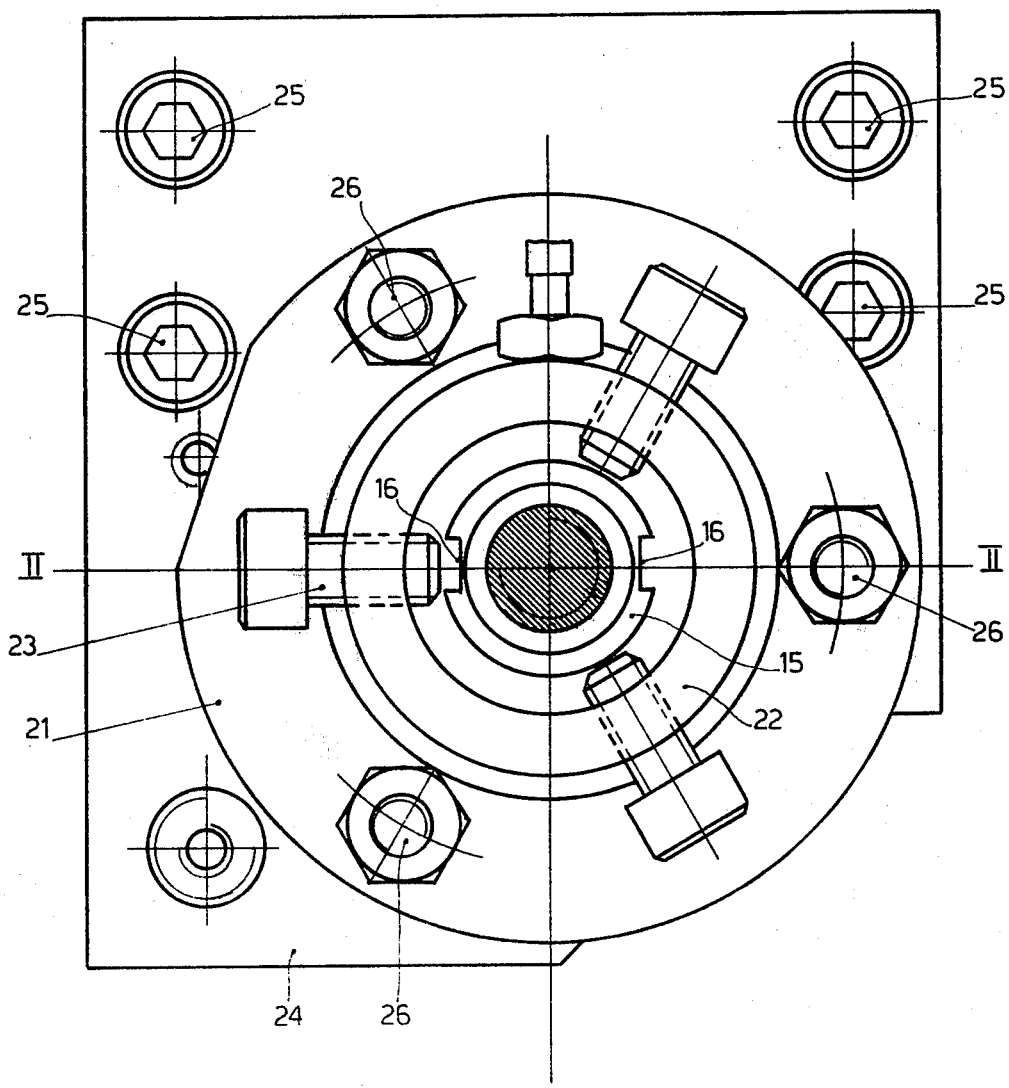
FIG. 3 is a plan view on line III—III of FIG. 2.

As illustrated in FIG. 3, bolts 26 are circumferentially distributed between the flange 21 and the plate 24 in such a manner that the bolts 26 extend parallel to plunger 11. Consequently the axis A of the durometer will also be parallel or coaxial with the axis A' of the plunger 11.

For a non-coaxial orientation position of the axis A of the durometer relative to axis A of the plunger 11, a flange 21 is simply lengthened, generally on one side of the flange 21, and preferably on the one side which is opposite the support structure 1. Holes 28 will be provided in positions further from the plunger 11 so that the axis A of the durometer 5 is parallel to and is displaced in an axial durection from axis A'.

Other mechanisms can be substituted for the bolts 26 and screw nuts 30, since the inventive concept pertains to means for providing the suspending effect and the restoration of the defined single orientation of the axial position of the durometer 5 rather than only to the specific components herein described as providing such effects. Similarly, other resilient means could be substituted for the coil springs 32.

Plunger 36 of the durometer receives the load generated by cylinder 2. Plunger 36 has a threaded axial hole opening into which is screwed a threaded stem 37. Threaded stem 37 has an upper end defined by head 38 which is preferably convexly shaped or rounded at its top and sides.

Stem 37 is tightened up to annular abutment 39 which abuts against the upper end of plunger 36.

Head 38 is positioned in a cylindrical seat 40 which is fixed to flange 21 and which has a planar lower end 62 and a planar seat bottom 61, each planar part 61, 62 being perpendicular to the axis A of plunger 36. The inner diameter of the seat 40 is equal to the maximum outer diameter of the rounded, convexly shaped head 38.

Head 38 can be oriented only in a single axial orientation position which is specifically determined by the degree to which the nuts 30 are screwed on the bolts 26. This head 38 is also generally spaced from the bottom 61 of seat 40 due to the constant springback force exerted by compressed springs 32.

The head 38 and seat 40 are rigid parts which together form a joint in which each part is capable of movement relative to the other part. As illustrated in FIG. 2, the head 38 and eat 40 together form a ball and socket joint since the head 38 is rounded. However, a ball and socket connection is not required to form the inventive arrangement. This is an articulation joint. The articulation joint transmits the applied load from plunger 11 to the durometer 5, permits axial displacement of the head 38 relative to the seat 40 and allows free inclination of the durometer 5 relative to the axis A' of plunger 11.

This free inclination is critical to store the defined single orientation position. Due to moment engenered as load is transmitted to the durometer 5, the support structure 1 is resiliently deformed so that axis A is reoriented. The free inclination restores the single orientation position of the durometer 5 relative to the support structure 1. When the support structure axis A returns to its previous orientation, free inclination allows the durometer 5 and its indentor point 7 to follow, to thereby again restore the single orientation position relative to the support structure.

The mechanism of this articulation joint 38, 40 shall now be explained. As the coil springs 32 spring back to their previously held position and the screw nuts 30 act as a detent, the joint maintains the durometer 5 in a single position. In this position, the head 38 of the articulation joint is kept spaced from the bottom 61 of the seat 40. The preloading operation begins first. The cylinder 2 then is actuated to urge the plunger 11 downwardly. The assembly formed by the joint and the durometer 5 descends together with the plunger 11. The indentor point 7 of the durometer is thereby contacted with a surface to be tested. As the indentor point 7 is further pressed, it retracts upwardly until reference plane 7' abuts the surface. This establishes the preload in the instrument.

If the preload is greater than the springback force of coil springs 32, then these coil springs are elongated in the downward direction. On the other hand, if the preload is less than this force of the springs 32, then the coil springs 32 are only downwardly elongated when the plunger 11 continues to descend after the reference plane 7' has been brought into abutment with the surface.

As the coil springs 32 are extended downwardly, the flange 21 is pulled downwardly. As the screw nuts 30 are detached from the upper face of flange 21, the constraints defining the single orientation position of the durometer axis A relative to axis A' are thereby removed; consequently, durometer 5 is free to incline in such cases where a force is established which is eccentric relative to the axis A of the durometer 5. The mechanism of this free inclination involves the loosely fitting bolts 26 also freely inclining within their holes 27.

These eccentric forces are especially engendered when the bottom 61 of seat 40 presses against head 38. The plunger 11 then transmits all of the applied load to the head 38 to thereby press the indentor point 7 against the surface.

But this application of the major load causes the support structure 1 to be resiliently deformed (resilient deformation may also be caused in a support on which the surface rests). The deformation produces eccentric forces; the eccentric forces tend to cause the indentor point 7 to slide on the surface being tested—unless the original axial relationship of durometer to support structure is restored.

A significant benefit achieved by incorporating an articulation joint within a durometer assembly is that these eccentric forces are not transmitted through the durometer 5. Instead, the effect of these eccentric forces is to merely cause an angular repositioning of durometer axis A, the repositioning having the effect of restoring the original single orientation position; this angular repositioning maintains a completely axially directed transmission of the applied load.

The durometer 5 may be used with a vertical axis, as illustrated in FIG. 1, with an inclined axis or particularly with a horizontal axis.

Where the axis is vertical, the weight of the durometer 5 is supported by flange 21. Where the axis is not vertical, the weight of the durometer must be balanced in order to avoid different loads on the coil springs.

With a horizontally oriented axis of the cylinder 2 and a supporting structure 1 oriented vertically along the dashed arrow F, a telescopic rod 41 is provided. A spring 42 is coiled around rod 41, this spring 42 has a springback force which tends to balance the weight of the durometer 5 to thereby permit the coil springs 32 to maintain symmetrical springback.

Rod 41 is interposed between durometer 5 and a side portion 1' of the supporting structure 1, and has a cap 43 which abuts the durometer and is pressed to such abutment by the spring 42. The cap includes an outward planar face which is actually where the abutting occurs. Due to the planar shape of this side of the cap, the durometer can rest or slide thereagainst.

It will be understood that each of the elements described above, or two or more together, may also find a useful application in other types of constructions differing from the types described above.

While the invention has been illustrated and described as embodied in an improved durometer, it is not intended to be limited to the details shown, since various modifications and structural changes may be made without departing in any way
present invention.

Without further analysis, the foregoing will so fully reveal the gist of the present invention that others can, by applying current knowledged, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A durometer, comprising in combination, an indentor point for penetrating under pressure of an applied load a surface being tested for hardness, said indentor point having an axis; load generating means for generating a load; a support structure connected to said load generating means; applying means having an axis and connected to said load generating means and passing through said support structure for transmitting the load to said indentor point in the axial direction thereof, said support structure including a flange extending normal to the axis of said applying means and being rigidly connected to said applying means; an articulation joint connected at one end to a portion of said support structure and at an opposite end to said indentor point to thereby maintain the indentor point at least substantially free from transmission of movement from said support structure, whereby moment engendered in said support structure during application of the load to said indentor point is kept from interfering with further transmission of the load; and suspending means connected to other portions of said support structure for suspending said indentor point therefrom, said suspending means including detent means for defining a first position of said indentor point relative to said support structure and resilient biasing means between said detent means and said indentor point for applying a force for biasing said indentor point in said position.

2. The duroeter defined in claim 1; further comprising a durometer body on said indentor point for receiving transmitted load directly from said applying means and being located between said indentor point and said flange, said resilient biasing means being interposed between said flange and said durometer body.

3. The durometer defined in claim 2, said flange having a plurality of apertures extending axially therethrough, and said suspending means comprising a plurality of at least substantially parallel bolts each having a free threaded end, said bolts extending from said durometer body and through a respective one of the apertures of said flange with the respective free ends protruding therefrom, and a plurality of screw nuts each being connected to a respective one of the free ends of said bolts.

4. The durometer defined in claim 3, said resilient biasing means being a plurality of coil springs each of which is wound around a respective one of said bolts.

5. The durometer defined in claim 4, said suspending means connecting said durometer body to said flange in such a manner that the axis of said indentor point is horizontally spaced from and is parallel to the axis of said applying means.

6. The durometer defined in claim 4, said suspending means connecting said durometer body to said flange in such a manner that the axis of said indentor point is coaxial with the axis of said applying means.

7. The durometer defined in claim 2, said articulation joint comprising a head fixed to said durometer body and having rounded lateral and end suraces, and a seat connected to a portion of said flange which faces said durometer body and having sufficient size and depth to permit entry of said head.

8. The durometer defined in claim 2, said applying means having a horizontally extending axis; further comprising balancing means for balancing the weight of said durometer body so as to hold the axis of said indentor point in a horizontally extending position.

9. A durometer, comprising in combination an indentor point for penetrating under pressure of an applied load a surface being tested for hardness; load generating means for generating a load; a support structure connected to said load generating means; applying means connected to said load generating means and passing through said support structure for transmitting the load to said indentor point; suspending means connected to said support structure for suspending said indentor point therefrom, said suspending means indirectly transmitting the load on said indentor point only until said load reaches a predetermined level; and an articulated joint operatively connecting said indentor point to said load generating means for transmitting the load directly on said indentor point only after the load generated by said load generating means exceeds said predetermined level.

* * * * *